United States Patent
Fink et al.

(10) Patent No.: US 7,670,048 B2
(45) Date of Patent: Mar. 2, 2010

(54) DRIVE UNIT FOR X-RAY SYSTEM

(75) Inventors: Henning Fink, Ammersbek (DE);
Horst-Hartwig Schwieker, Hamburg (DE); Uwe Meyer-Douque, Hamburg (DE); Janos Csikos, Budapest (HU);
Gyorgy Medgyesi, Budapest (HU)

(73) Assignee: Koninklijke Philips Electronics N.V, Eindhoven (NL)

( * ) Notice: Subject to any disclaimer, the term of this patent is extended or adjusted under 35 U.S.C. 154(b) by 322 days.

(21) Appl. No.: 11/719,553

(22) PCT Filed: Nov. 22, 2005

(86) PCT No.: PCT/IB2005/053860

§ 371 (c)(1),
(2), (4) Date: May 17, 2007

(87) PCT Pub. No.: WO2006/085156

PCT Pub. Date: Aug. 17, 2006

(65) Prior Publication Data

US 2009/0154653 A1    Jun. 18, 2009

(30) Foreign Application Priority Data

Nov. 23, 2004 (EP) .................. 04106004

(51) Int. Cl.
*H05G 1/02* (2006.01)
(52) U.S. Cl. .................................... 378/197
(58) Field of Classification Search .......... 378/193–198
See application file for complete search history.

(56) References Cited

U.S. PATENT DOCUMENTS

| 4,435,830 A | * | 3/1984 | Suzuki et al. ............... 378/197 |
| 5,572,567 A | | 11/1996 | Khutoryansky et al. ..... 378/197 |
| 5,870,450 A | | 2/1999 | Khutoryansky et al. ..... 378/197 |
| 6,027,247 A | | 2/2000 | Tachi et al. ................. 378/196 |

FOREIGN PATENT DOCUMENTS

| DE | 4008415 A1 | 2/1991 |
| EP | 0068929 A2 | 1/1983 |
| WO | WO9637088 A1 | 11/1996 |
| WO | WO03071948 A1 | 9/2003 |

* cited by examiner

*Primary Examiner*—Courtney Thomas

(57) ABSTRACT

The invention relates to a drive unit (12) for vertical or horizontal movement of a component (7) of a diagnostic X-ray device (1), comprising a motor and gear unit (14), a pulley (10) mounted on a drive shaft (13) of the motor and gear unit (14), and traction means (9), e.g. a rope or a drive belt, wound around the pulley (10), the component (7) to be moved being either attached to the traction means (9) or connected with the drive unit (12). In order to provide a drive unit (12) enabling collision detection, emergency stop functionality, and improved handling with regard to control of the motion of the component (7) by an operator of the X-ray device (1), the invention proposes that the motor and gear unit (14) is rotatable about the axis of the drive shaft (13) against the elastic force of a balancing spring (15), wherein provision is made for a rotation sensor (17,24), which rotation sensor (17,24) is adapted for detecting a rotation of the motor and gear unit (14) and for generating a corresponding rotation detection signal.

7 Claims, 2 Drawing Sheets

DRIVE UNIT FOR X-RAY SYSTEM

Figure 1:
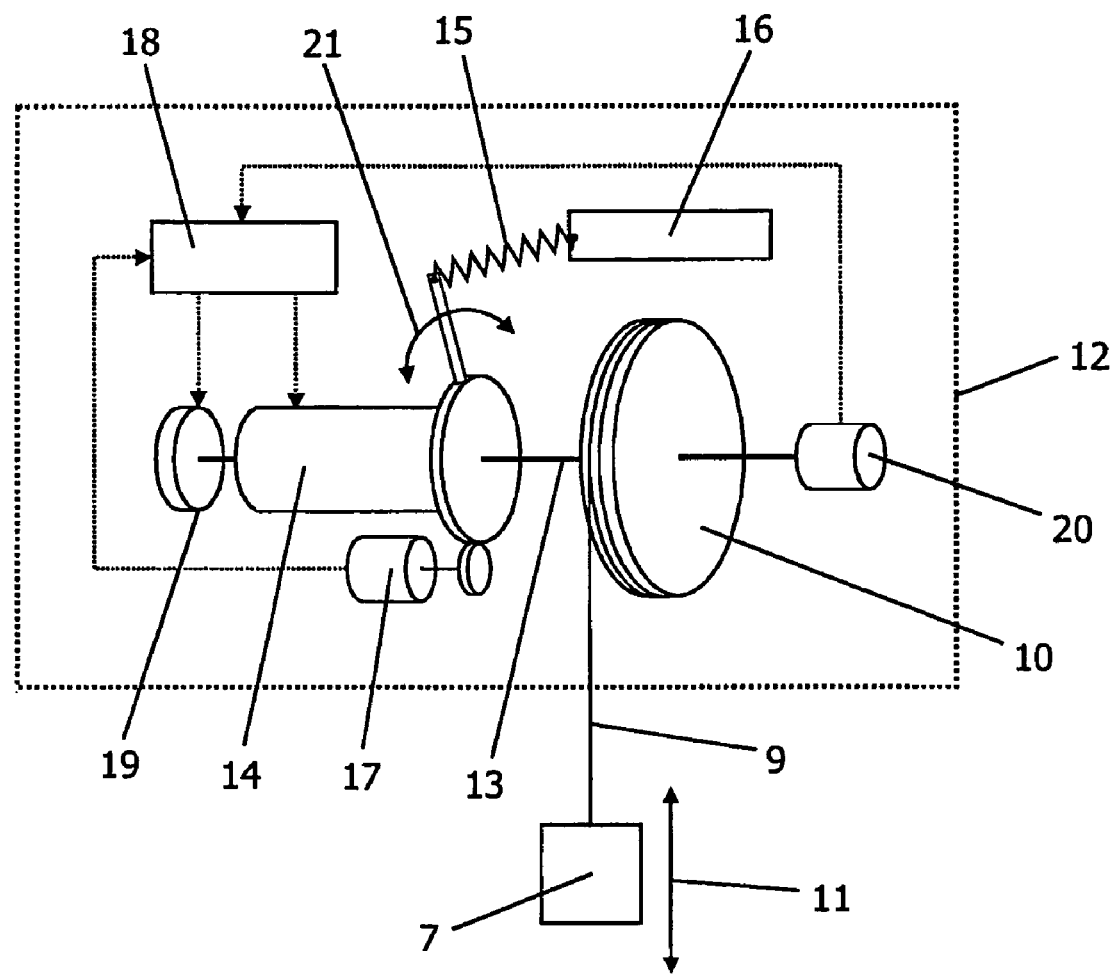

The invention relates to a drive unit for vertical or horizontal movement of a component of a diagnostic X-ray device, comprising a motor and gear unit, a pulley mounted on a drive shaft of the motor and gear unit, and traction means wound around the pulley, the component to be moved being either attached to the traction means or connected with the drive unit.

Furthermore the invention relates to an X-ray apparatus comprising an X-ray source, an X-ray image detector in confronting relation to the X-ray source, and at least one drive unit for vertical and/or horizontal movement of the X-ray source or the X-ray image detector.

In the field of medical diagnostic imaging, and particularly in the field of X-ray fluoroscopy and radiography, a wide spectrum of equipment is nowadays commercially available. In a conventional X-ray system, as it is for example known from EP 0 068 929 A2 or U.S. Pat. No. 4,435,830, the patient is supported during an examination on a radiographic-fluoroscopic table comprising an X-ray image detector, e.g. a normal X-ray film, an electronic X-ray image intensifier, or a digital X-ray flat detector. An overhead X-ray source, e.g. a conventional X-ray tube, directs a beam of radiation through the patient to the X-ray image detector underneath the patient. The X-ray source is mounted on a tube crane to support the X-ray source and to enable vertical and horizontal movement of the X-ray source. Depending on the respective part of the body of the patient to be examined, horizontal and vertical movability of the X-ray source and/or the X-ray image detector relative to the patient is necessary. The tube crane of the conventional X-ray apparatus is extensible and contractible by means of telescoping sections. These telescoping sections are telescopically movable by a wire rope wound around a pulley. The X-ray tube can be lifted either automatically by means of a motor. In this case the pulley is mounted on a drive shaft of a gear box, wherein the gear box and the motor form a remotely controllable motor and gear unit of the known system. Other X-ray systems are known, in which the X-ray tube can be lifted manually. With these systems usually a balancing of the heavy weight of the X-ray tube is effected for example by counterweights or by a gas spring as it is employed in accordance with the above-cited EP 0 068 929 A2. The known systems usually further employ ceiling suspended guide rails in two perpendicular directions for enabling horizontal movements of the X-ray tube. Also the horizontal motion can be effected with the known systems either manually or automatically by means of drive belts, wire ropes, or any other suitable traction means and corresponding motor and gear drives.

It is a drawback of both the vertical and horizontal drive units of the known X-ray systems that they do not provide detection of collisions, e.g. of the vertically moving X-ray tube with the body of the patient supported on the radiographic table, and corresponding emergency stop functionalities. A further disadvantage is that the known systems can be operated only in two different modes, either manually, i.e. without the driving force of the motor and gear unit, or automatically by means of the remotely controllable motor. Manual handling is sometimes difficult for a user operating the X-ray apparatus because of the high intertial mass of the X-ray tube to be moved, which is requiring a corresponding high muscular strength of the user. On the other hand, the motion of the X-ray tube is controllable in the motor driven mode only by means of some kind of remote control unit of the known systems, e.g. in the form of a joystick or other similar input device. The users operating the known X-ray systems often feel uncomfortable with remotely controlling the motion of the X-ray tube in this way, because the motion control is indirect without any sensible feedback. Furthermore, remote control of the motion is sometimes not sufficiently precise for positioning the X-ray tube as required by the respective examination procedure.

Therefore it is readily appreciated that there is a need for an improved drive system for an X-ray device for enabling horizontal or vertical movement of components of the X-ray device. It is the object of the invention to provide such a drive unit enabling collision detection, emergency stop functionality, and improved handling with regard to control of the motion of the component by a user operating the X-ray device.

In accordance with the present invention, a drive unit for vertical or horizontal movement of a component of a diagnostic X-ray device is disclosed comprising a motor and gear unit, a pulley mounted on a drive shaft of the motor and gear unit, and traction means wound around the pulley, wherein the component to be moved is attached to the traction means or connected with the drive unit. The motor and gear unit is rotatable about the axis of the drive shaft against the elastic force of a balancing spring, wherein provision is made for a rotation sensor, which rotation sensor is adapted for detecting a rotation of the motor and gear unit and for generating a corresponding rotation detection signal.

With the drive unit according to the invention, the respective component of the X-ray device, e.g. the X-ray source or the X-ray image detector, is either attached to the traction means, e.g. a rope or a drive belt, and moved by the motive force of the motor and gear unit. It is also possible that the moving component is directly connected with the drive unit, such that it moves together with the drive unit along the spatially fixed traction means. The latter variant is particularly suitable for enabling horizontal movement of the respective part of the X-ray device. The motor and gear unit, which can be contained in a corresponding shared housing of the motor and the gear box, is not firmly mounted but is rotatable about the axis of the drive shaft of the motor and gear unit. The motor and gear box can thus be rotated against the elastic force of the balancing spring. For this purpose, one end of the spring can be connected to the housing of the motor and gear unit, while the other end is secured to the main frame of the X-ray apparatus. In general, the balancing spring can be a tension spring or a compression spring or even an arrangement of two or more separate springs.

With regard to vertical motion of the component, initially two forces, namely the weight force of the component in one direction and the elastic force of the spring, are in equilibrium. When an additional external force is applied to the component, the equilibrium position changes and the spring will be stretched either more or less depending on the direction and magnitude of the external force. This results in a corresponding rotation of the motor and gear unit. The rotational movement of the housing of the motor and gear unit is then detected by means of the rotation sensor which generates a corresponding rotation detection signal.

In case of horizontal movements, the equilibrium angular position of the motor and gear unit is solely determined by the arrangement of the balancing spring. When an external force is exerted on the horizontally moving component, the equilibrium changes, a rotational movement of the motor and gear unit occurs, and again a corresponding rotation detection signal is generated.

The rotation detection signal can advantageously be used directly to control the operation of the motor and gear unit. For this purpose, the rotation detection signal can be supplied to a corresponding motor control unit of the system. In this way, a servo control of the moving component of the X-ray device can be realized.

It is for example possible in accordance with the invention to lift or lower the X-ray tube of the X-ray apparatus as desired depending on the (small) external force the operator of the X-ray device applies manually to the X-ray tube. Thereby the lifting or lowering speed can be controlled such that it is proportional to the magnitude and/or the duration of applied external force. A minimum muscular strength is required in this servo mode of operation, while a precise and direct motion control is provided. An important advantage of this servo mode is that the external controlling force can be applied anywhere on the moving component of the X-ray apparatus without restriction to a certain handle portion of the moving part. With the servo control of the invention a remote control unit for controlling the motor and gear unit is not required at all. A further advantage is that because of the physical properties of the balancing spring the external operating force is directly measured which allows for a corresponding control of the operation of the motor and gear unit. Thereby the motion control is much more direct than with the known remote control units and gives the operator of the X-ray device a good feedback.

Furthermore, the drive unit of the invention intrinsically detects any collision. If a collision occurs anywhere on the moving part of the X-ray device, the collision force counteracts the external operating force, the housing of the motor and gear unit rotates back into the equilibrium position, and the system stops immediately.

In accordance with a preferred embodiment of the drive unit of the invention, the rotatable motor and gear unit is further spring-loaded by additional preloading springs defining an equilibrium angular position of the motor and gear unit. The additional preloading springs hold the motor and gear unit in the equilibrium angular position with a certain amount of initial load. With this embodiment of the invention, the motion can be remotely controlled by means of some sort of remote control unit, e.g. a joystick device, wherein the direction and the speed of rotation of the motor is independent of any external force applied to the moving part. However, if the external force exceeds a certain magnitude predetermined by the tension of the additional preloading springs, an angular movement of the housing of the motor and gear unit takes places which is then detected by the rotation sensor of the drive unit. Collisions occurring anywhere on the moving component of the X-ray device can be detected in this way without needing separate collision sensors. The rotation sensor can be realized as a simple switch that is activated as soon as the housing of the motor and gear unit rotates out of the pre-defined equilibrium angular position. The signal of the switch can then directly be used to stop the system immediately in case of a collision. A further advantage of this embodiment of the invention is that collision forces are taken up to a large extent by compression or elongation of the springs such that the moving component is not driven into the colliding object with excessive force of the motor and gear unit before the system stops.

With the drive unit of the invention it is advantageous to make provision for a position sensor for detecting the position of the moving component of the X-ray apparatus. This position sensor can be connected to the motor control unit such that the signal of the position sensor can be used together with the signal of the rotation signal for determining the direction and speed of rotation of the motor and gear unit. The position sensor can for example be a potentiometer mounted on the drive shaft of the pulley or a suitable encoder mounted on the drive shaft of the motor. In this way, the position sensor supplies an analog or digital signal representing the horizontal or vertical position of the moving component of the X-ray apparatus.

The following drawings disclose preferred embodiments of the present invention. It should be understood, however, that the drawings are designed for the purpose of illustration only and not as a definition of the limits of the invention. In the drawings FIG. 1 shows an embodiment of a drive unit for hand operated motion of a component of an X-ray apparatus according to the invention, FIG. 2 shows an embodiment of a drive unit for remotely controlled motion in accordance with the invention, FIG. 3 illustrates an X-ray device according to the invention.

Figure 3:
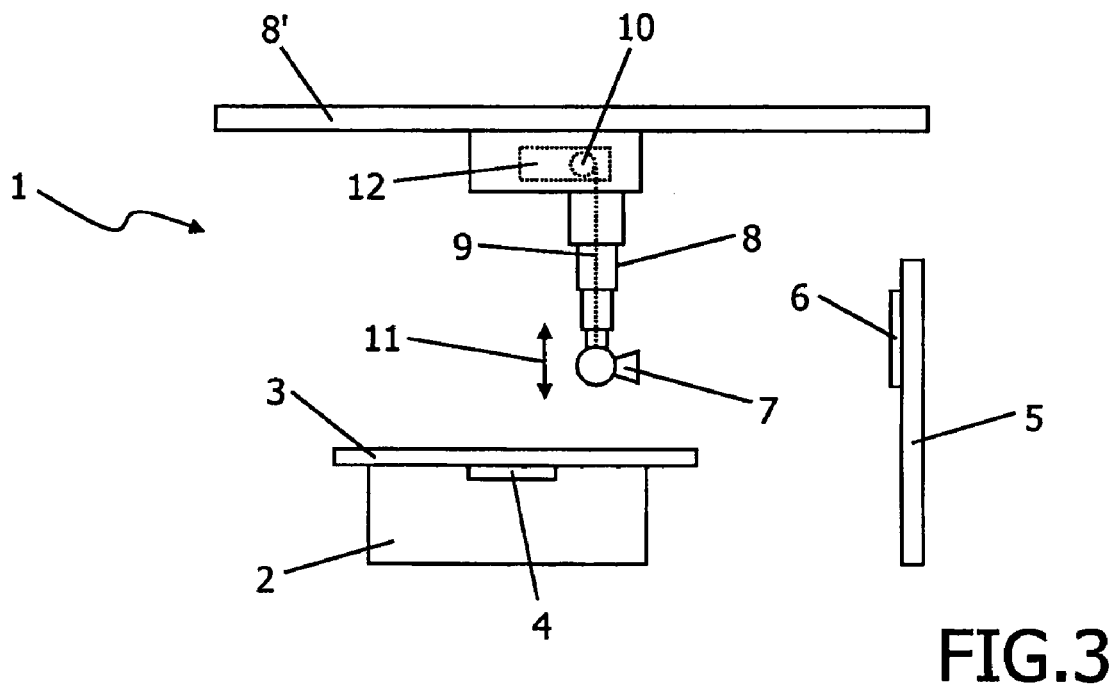

With reference to FIG. 3, an X-ray device 1 in accordance with the present invention is described. The X-ray device 1 comprises a table 2 with a table top 3 for supporting a patient during an examination. The table 2 has a receptacle 4 for an X-ray film. Furthermore, provision is made for a wall stand 5 also comprising a receptacle 6 for an X-ray film. This wall stand 5 can be used for examination of a patient in a standing position. An overhead X-ray source 7 directs a beam of radiation through the patient to the X-ray film underneath or behind the patient. The X-ray source 7 is mounted on a tube crane 8 to support the X-ray source 7 and to enable vertical and horizontal movement of the X-ray source 7. The tube crane 8 of the depicted X-ray apparatus 1 is extensible and contractible by means of telescoping sections. These telescoping sections are telescopically movable by a wire rope 9 guided through the tube crane 8 and wound around a pulley 10. The X-ray source can be lifted or lowered (as indicated by arrow 11) by means of a drive unit 12. The tube crane 8 is attached to ceiling-mounted guide rails 8' for enabling horizontal movement.

FIG. 1 shows an embodiment of a drive unit 12 in accordance with the invention enabling a servo mode of operation. As already described with reference to FIG. 3, the X-ray source 7, as a vertically moving component of the X-ray device 1, is suspended on a wire rope 9. This wire rope 9 is wound around the pulley 10, which is mounted on a drive shaft 13 of a motor and gear unit 14. The housing of the motor and gear unit 14 is not firmly secured to the frame structure of the X-ray system but is rotatable about the axis of the drive shaft 13. A balancing spring 15 connects the housing of the motor and gear unit 14 to a main frame structure 16 of the X-ray apparatus such that the motor and gear unit 14 is rotatable against the elastic force of the balancing spring 15. Provision is made for a rotation sensor 17, a potentiometer in the depicted embodiment, adapted for detecting a rotation of the housing of the motor and gear unit 14. The detection signal generated by the rotation sensor 17 is supplied to a motor control unit 18. The motor control unit 18 controls the speed and the direction of rotation of the motor of the motor and gear unit 14. Furthermore, the motor control unit 18 is connected to a brake 19 for actively slowing down the vertical motion of the X-ray source 7 if required. The brake 19 is also required to compensate for the weight force of the X-ray source 7 when the motor of the motor and gear unit 14 is deactivated. An additional potentiometer 20 operating as a position sensor is mounted on the drive shaft 13. By means of potentiometer 20 the vertical position of the X-ray source 7 can be detected. The signal generated by the position sensor 20 is supplied to the control unit 18 as well. On the basis of the rotation detection signal generated by rotation sensor 17 and the signal of the position sensor 20, the motor control unit 18 can calculate the necessary rotation speed and direction for the desired vertical motion of the X-ray source 7. As already described above, two forces, namely the (weight) force of the X-ray source 7 in one direction and the elastic force of the balancing spring 15 are in equilibrium. When an additional external force is applied to the X-ray source 7, as for example a manual force exerted on the X-ray source 7 by an operator of the X-ray device, the equilibrium position changes and the spring 15 will be stretched either more or less depending on the magnitude and the direction of the external force. This results in a corresponding rotation of the motor and gear unit 14 as indicated by arrow 21. The rotational movement of the housing of the motor and gear unit 14 is then detected by means of the rotation sensor 17, which generates the corresponding rotation detection signal. Depending on the rotation detection signal the motor control unit 18 controls the motor and gear unit 14 such that the X-ray source 7 is lowered or lifted as desired by the operator.

Figure 2:
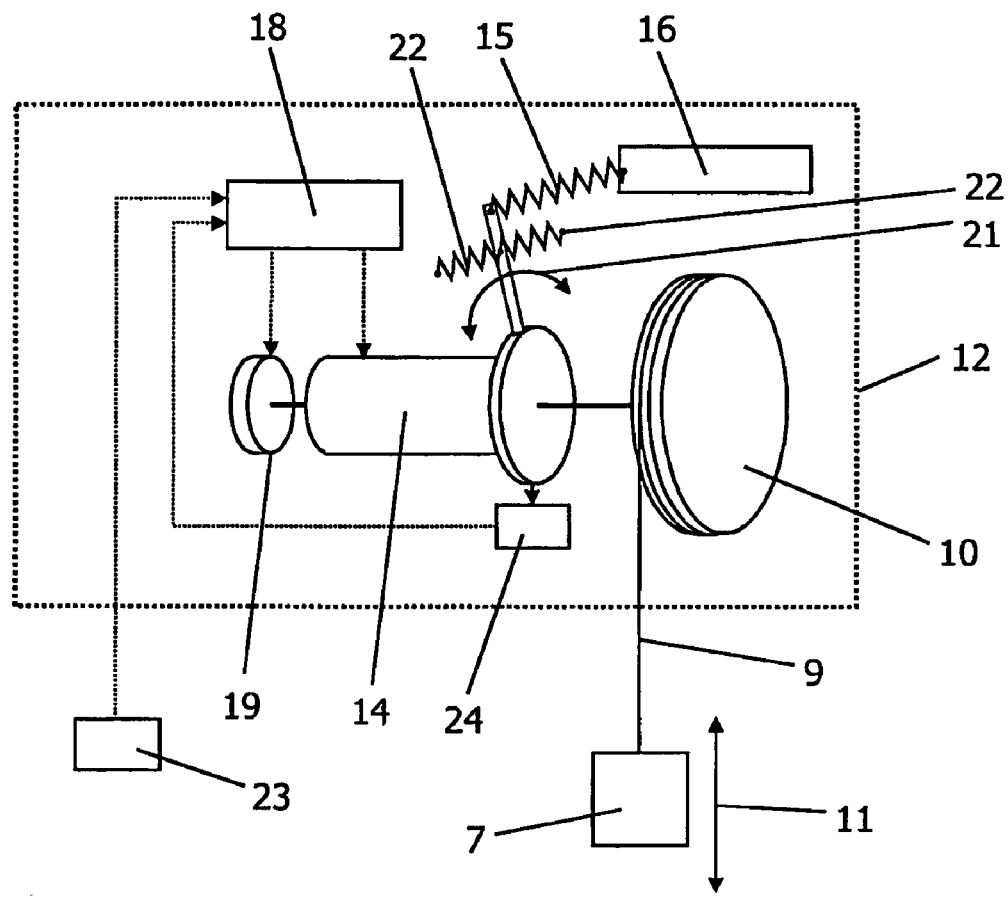

With reference to FIG. 2, an embodiment of the present invention is described for remotely controlled motion of the X-ray source 7. The main difference with respect to the embodiment of FIG. 1 is that provision is made for additional preloading springs 22. The motor and gear unit 14 is spring-loaded by these additional springs 22 which are defining an equilibrium angular position of the motor and gear unit 14. The vertical motion of the X-ray source 7 is remotely controlled by means of a remote control unit 23, wherein the direction and the speed of rotation of the motor and gear unit 14 is independent of any external force applied to the moving part 7. However, if an external force occurs exceeding a certain magnitude pre-determined by the tension of the additional preloading springs 22, an angular movement of the housing of the motor and gear unit 14 takes places which is then detected by a rotation sensor 24 of the drive unit 12 depicted in FIG. 2. Collisions occurring anywhere on the moving component 7 of the X-ray device can be detected in this way. The rotation sensor 24 is a simple switch that is activated as soon as the housing of the motor and gear unit 14 rotates out of the pre-defined equilibrium angular position. The signal of the switch 24 is supplied to the motor control unit 18 and can thus be used to stop the system immediately in case of a collision.

The invention claimed is:

1. A drive unit for vertical or horizontal movement of a moving component of a diagnostic X-ray device, comprising a motor and gear unit, a pulley mounted on a drive shaft of the motor and gear unit, and traction means wound around the pulley, the moving component being either attached to the traction means or connected with the drive unit, wherein the motor and gear unit is rotatable about the axis of the drive shaft against the elastic force of a balancing spring, wherein the rotatable motor and gear unit is spring-loaded by preloading springs that define an equilibrium angular position of the motor and gear unit for detecting a collision occurring anywhere on the moving component, further comprising a rotation sensor adapted for detecting a rotation of the motor and gear unit for generating a corresponding rotation detection signal and for activating a switch to stop the movement when a collision is detected.

2. The drive unit of claim 1, wherein the rotation sensor is connected to a motor control unit for controlling the direction or speed of rotation of the motor of the motor and gear unit.

3. The drive unit of claim 1, further comprising a position sensor connected to the motor control unit for detecting the position of the moving component.

4. The drive unit of claim 1, wherein the rotation sensor is a potentiometer.

5. The drive unit of claim 1, wherein the rotation sensor is a switch.

6. An X-ray apparatus comprising an X-ray source, an X-ray image detector in confronting relation to the X-ray source, and at least one drive unit for vertical or horizontal movement of the X-ray source or the X-ray image detector, wherein the drive unit comprises a motor and gear unit, a pulley mounted on a drive shaft of the motor and gear unit, and traction means wound around the pulley, the X-ray source or the X-ray image detector being either attached to the traction means or connected with the drive unit, wherein the motor and gear unit is rotatably mounted on a main frame of the X-ray apparatus such that it is rotatable about the axis of the drive shaft against the elastic force of a balancing spring, wherein the rotatable motor and gear unit is spring-loaded by preloading springs that define an equilibrium angular position of the motor and gear unit for detecting a collision occurring anywhere on the moving component, wherein provision is made for a rotation sensor adapted for detecting a rotation of the motor and gear unit for generating a corresponding rotation detection signal and for activating a switch to stop the movement when a collision is detected.

7. The X-ray apparatus according to claim 6, further comprising a remote control unit enabling an operator to remotely control the vertical or horizontal motion of the X-ray source or the X-ray image detector.

* * * * *